United States Patent [19]
Jones et al.

[11] Patent Number: 5,679,819
[45] Date of Patent: Oct. 21, 1997

[54] CYSTINE-SILICONE COPOLYMERS AND THEIR USE FOR TREATING KERATIN SUBSTRATES

[75] Inventors: Roger Trevor Jones, Cuddington; Surinder Pall Chahal, Warrington, both of Great Britain

[73] Assignee: Croda International PLC, Great Britain

[21] Appl. No.: 627,121

[22] Filed: Apr. 3, 1996

[30] Foreign Application Priority Data

Apr. 4, 1995 [GB] United Kingdom ............ 9506926

[51] Int. Cl.⁶ .................................................. C07F 7/10
[52] U.S. Cl. .................. 556/418; 8/115.6; 8/128.3; 514/63; 424/70.11; 424/70.12; 424/70.122; 424/70.51; 424/78.03; 424/78.17
[58] Field of Search ................ 556/418; 514/63; 424/70.11, 70.12, 70.51, 70.122, 78.03, 78.17; 8/115.6, 128.3

[56] References Cited

U.S. PATENT DOCUMENTS

| | | | |
|---|---|---|---|
| 4,113,696 | 9/1978 | Williams et al. | 556/418 |
| 5,068,378 | 11/1991 | Halloran et al. | |
| 5,085,858 | 2/1992 | Halloran et al. | |

FOREIGN PATENT DOCUMENTS

| | | |
|---|---|---|
| 505854 | 9/1992 | European Pat. Off. |
| 1174528 | 7/1989 | Japan. |
| 5339132 | 12/1993 | Japan. |

*Primary Examiner*—Paul F. Shaver
*Attorney, Agent, or Firm*—Lerner, David, Littenberg, Krumholz & Mentlik

[57] ABSTRACT

A copolymer comprising cystine, or a derivative thereof, bonded to a silicon-containing group, wherein the silicon containing group is bonded to one or more other silicon-containing groups by siloxane groups. This polymer is useful for treating keratin-containing substrates.

17 Claims, No Drawings

CYSTINE-SILICONE COPOLYMERS AND THEIR USE FOR TREATING KERATIN SUBSTRATES

The invention relates to cystine-silicone copolymers and their use for treating keratin substrates, such as hair, nails, skin and wool. The invention also relates to a method of making cystine-silicone copolymers.

The keratin in such substrates are known to be stabilised by disulphide bonds between polypeptide chains, in the form of cystine residues. Cystine residues can be reduced to cysteine residues by the use of reagents such as a ammonium thioglycollate, sodium sulphite/bisulphite, thiolactic acid, glyceryl monothioglycollate, cysteine and cysteamine. Disulphide bonds can be reformed by oxidation using reagents such as hydrogen peroxide, or sodium bromate. Such reduction/oxidation processes form the basis of the commercially important cold permanent-wave treatments for hair in which disulphide bonds are broken and reformed in a new configuration. Cysteine treatment of wool has been claimed to be useful in imparting permanent-press characteristics to machine washable fabrics, based on a similar mechanism.

In the reduction/oxidation treatment applied to hair and wool keratin some of the cystine and cysteine residues are converted to cysteic acid, resulting in a loss of dry strength and, more particularly, vet strength of the fibres. Similar damage occurs in oxidative bleaching processes resulting in a general deterioration in the "condition" of the hair or wool. Temporary "conditioning" of the keratin fibre can be achieved using, for example, long chain fatty quats, cationic polymers, or silicones to treat the surface of the fibres. More-permanent conditioning is possible when the conditioning agent is capable of forming covalent bonds with the hair keratin. Examples of such agents are partially hydrolysed soluble keratins which contain cystine/cysteine residues in their molecules and are capable of forming disulphide links to the hair when included in a reduction/oxidation treatment.

Certain high molecular weight soluble keratin polypeptides can be considered to be polyfunctional in terms of thiol groups: such polypeptides are potentially capable of producing multiple disulphide bonding to hair and a consequent strengthening effect. However, such behaviour is largely restricted to the surface of the cuticle due to lack of penetration into the fibres. Conversely low molecular weight hydrolysed keratin may be capable of penetration through the cuticle into the cortex, but even with high cystine content will no longer be multifunctional or capable of a strengthening effect. For example, a keratin hydrolysate with a 5% cystine content and an average molecular weight of 100,000 Daltons will have, on average, approximately twenty ½ cystine residues per polypeptide molecule, whereas for the same keratin protein with an average molecular weight of 1000 Daltons only 20% of the polypeptides will have even one ½ cystine residue.

It will be apparent from the foregoing that a conditioning agent for keratin substrates which is capable of penetrating into the fibres and, at the same time, is capable of producing multi-disulphide links to the keratin through a polymeric chain would offer advantages over existing treatments for strengthening and conditioning the keratin fibres, in addition to any surface conditioning benefits.

We have now devised a new material which can be used as such a conditioning agent for keratin substrates.

Broadly, the invention provides a copolymer comprising units made up of cystine, or a derivative thereof, bonded to a silicon-containing component containing at least one siloxane link.

Thus, the invention provides a polymer comprising cystine, or a derivative thereof, bonded to a silicon-containing component, the silicon-containing group being bonded to one or more other silicon-containing group's by siloxane groups.

According to one aspect of the present invention, there is provided a copolymer containing units of formula:

where A is $HN-CH(COOR_x)CH_2-S-S-CH_2CH(COOR_y)NR_z$, $R_x$ and $R_y$ are the same or different and are hydrogen or an alkyl group, and B and B' represent silicon-containing groups: wherein the units are linked together by siloxane bonds, the groups B and B' are the same or different, the group B in each unit may be the same as or different from the group B in any other unit, and the group B' in each unit may be the same as or different from the group B' in any other unit.

$R_z$ is hydrogen or an amino-modifying group. The amino modifying group may be, for example, $R_w$ CO, where $R_w$ is an alkyl group, or $R_{w1}(R_{w2})(R_{w3})N^+-CH_2-CH(OH)-CH_2-$, where $R_{w1}$, $R_{w2}$ and $R_{w3}$ are the same or different alkyl groups.

The polymers of the invention are polyfunctional in terms of cystine residues can be produced with molecular weight distributions such that the lower molecular weight species are able to penetrate into keratin substrates and when they have been produced in solution are generally capable of further polymerisation on drying.

In the cystine-silicone copolymers of the invention, the silicone is covalently bonded to the amino groups of the amino acid cystine to form the unit [—B—A—B'—]. These "units" are further linked together by siloxane bonds to form a copolymer. The groups B and B' may themselves contain one or more siloxane links. Additional and more significant condensation polymerisation generally occurs when a solution of the cystine-silicone copolymer is concentrated by removal of solvent.

It will be appreciated that the copolymers of the invention will have a terminal group at the end of the polymer chain. This terminal group may be cystine or a derivation thereof, or may be a silicon-containing group.

The cystine component is preferably cystine itself, but may be a derivative of cystine in which one of the amino groups or one or both of the carboxyl groups have been chemically modified. In the copolymer the cystine may also be in the reduced form as cysteine, or as the Bunté salt.

The initial step in the production of cystine-silicone copolymers of the invention is the reaction of an organofunctional silicone with the amino groups of cystine, or the cystine derivative. At least one, and preferably more than one of the cystine amino groups must be reacted in this way. Suitable reactive groups on the silicone include epoxide, sulphonyl halide, acyl halide, anhydride and aldehyde groups, but other reactive groups may be used instead. The "silicone" component may be any compound which contains a siloxane group (Si—O—Si), or any silane capable of forming a siloxane in-situ by condensation of silanol (Si—OH) groups, or any alkoxysilane or halosilane which hydrolyses to form a corresponding silanol and then condenses to form a siloxane group, provided that the silicone contains at least one silanol group, or group which hydrolyses to form a silanol group, in its structure.

The second stage in the production of the cystine-silicone copolymer is the joining up of the units to each other or to other silicon-containing units reactive herewith to form linking siloxane groups. Polymerisation of the product from reaction of the organofunctional silicone with cystine can be effected by condensation of silanol groups to form siloxane bonds. This polymerisation condensation reaction may follow the initial reaction of organofunctional silicone with cystine or may take place concurrently, depending upon the reaction conditions. Similarly, the degree of polymerisation may be controlled by selection of reaction conditions.

The organofunctional silicone/silane reactant is preferably soluble in a solvent common to cystine for efficient reaction. Water or aqueous/alcohol solutions are generally preferred.

In order to achieve the desired degree of reaction and cross-linking it is highly desirable to control carefully the conditions for reaction of the organofunctional silicone/silane with cystine. For reaction of the cystine amino groups to occur it is advantageous for the pH to be above pH 7 and preferably within the pH range 8 to 11.5. Reaction may be carried out at ambient temperature, but an elevated temperature is preferred. The invention may be carried out at temperatures in the range 10° to 80° C., but more preferably a temperature of 40°–80° C. is used.

The degree of polymerisation is influenced by solution concentration: higher concentration resulting in increased degree of condensation polymerisation.

More complex copolymers can be achieved by silanol condensation between the cystine-silicone copolymers and other silanol-containing compounds such as dimethyl dihydroxy silane or its condensation products, silanol terminated polydimethyl siloxanes, or protein-silicone copolymers (as described in EP-A2-0540357): or by partial replacement of mono-organofunctional silanes by di-organofunctional silanes such as compounds IV and V set out below.

Cystine may represent approximately 2% to 80% of the copolymer, but more preferably 20% to 70% by weight.

The inclusion of the cystine-silicone copolymer into cosmetic formulations can be at any desired level, but it is generally preferred to use from 0.1 to 5% w/w of the copolymer.

In one embodiment the organofunctional silanes have the structure:

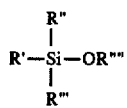

where:

R' is a group containing an amino-reactive group capable of reacting with the amino group in the cystine or the cystine derivative.

R" and R'" are the same or different and are an alkyl group or an alkoxy group or R"" is hydrogen or an alkyl group.

Examples of suitable organofunctional silanes containing an epoxy group are illustrated by below.

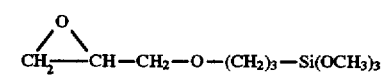

I

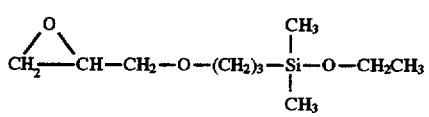

II

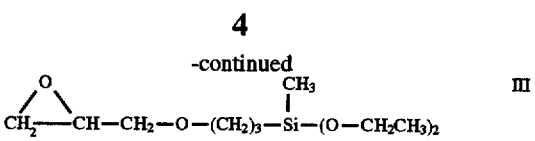

III

The organofunctional silanes IV and V discussed above are:

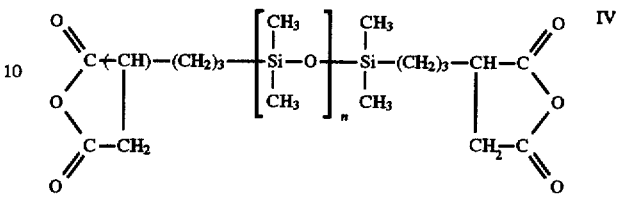

IV where n=1–50, preferably 30–40.

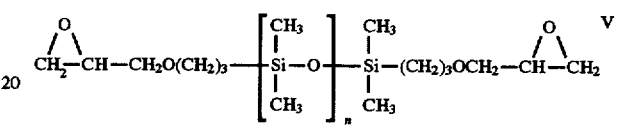

V where n=1–50, preferably 12–25.

The chemical structure of the cystine silicone copolymers according to the invention are likely to be complicated, but can be illustrated by the general simplified structure IV indicated below.

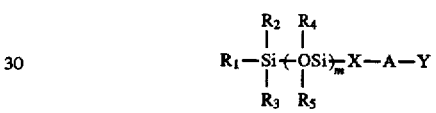

where:

X is a link group resulting from the reaction of an amino group on the cystine or cystine derivative with an amino reactive group of the silicon-containing group; R, in the group A, is H or CH$_2$CH$_3$:

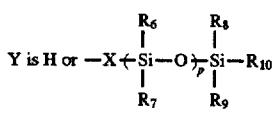

or an amino-modifying group;

R$_1$ to R$_{10}$ are the same or different, and are CH$_3$, OH or Z, where Z is one of:

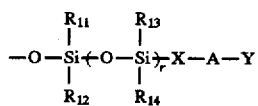

or

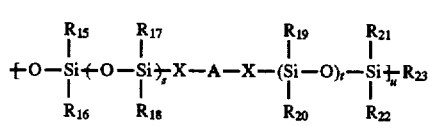

or

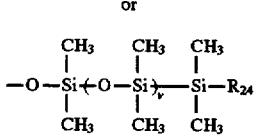

where R$_{11}$ to R$_{22}$ are the came or different and are CH$_3$, OH or Z, and R$_{23}$ and R$_{24}$ are CH$_3$ or OH.

and m is from 0–100 p is from 0–100 r is from 0–100 s is from 0–100 t is from 0–100 u is from 0–100 v is from 0–100

Values of r,s,t,u and v may be the same or different. At least one of the Groups $R_1$ to $R_{10}$ should contain at least one Z group containing an A group.

The cystine-silicone copolymers according to the invention as described above have been found to exhibit physical and chemical properties which make them valuable for cosmetic formulations used for conditioning hair, skin or nails and for textile applications in the treatment wool.

In order that the invention may be more fully understood the following examples are given by way of illustration only.

EXAMPLE 1

A cystine-silicone copolymer was prepared by reaction of organofunctional silane I with cystine, according to the following procedure.

50 g L-cystine was dispersed in 450 g deionised water and the pH raised to 10 using 47% sodium hydroxide solution. The temperature was raised to 60° C. and then 49.1 g silane I was added over a period of 2 hours whilst stirring and maintaining the pH at 10 by addition of further sodium hydroxide, and maintaining the temperature at 60° C. After a further 4 hours the product was filtered to give a clear solution of the copolymer.

The degree of modification of cystine amino groups was determined as 68% based on a modified formol titration procedure.

EXAMPLE 2

A reduced form (as the Bunté salt) of the cystine copolymer was prepared as follows.

12 g $Na_2SO_3.7H_2O$ was dissolved in 100 g copolymer solution. The solution remained clear on reducing the pH to 7.

EXAMPLE 3

The molecular weight distributions of the reduced and non-reduced forms of the copolymer were determined by size exclusion hplc using a GMPWXL column and polystyrene sulphonate molecular weight standards and compared with cysteine. The cysteine elution peak corresponded to an approximate molecular weight of 150 (compared with actual value of 122). The major peak for cystine silicone copolymer occurred at approx. 16,000 Daltons, with a smaller peak at approx. 1000 Daltons. For the reduced copolymer, the major peak occurred at approx. 1000 Daltons with a smaller peak at 16,000 Daltons. No peak or shoulder was observed corresponding to free cysteine.

This data showed that a copolymer had been produced containing disulphide links which could be broken using sulphite, a reducing agent commonly used in the cosmetic and textile industries. The reduced form of the copolymer contained a significant proportion of molecules small enough to penetrate into hair.

EXAMPLE 4

5% active solutions of copolymer in 6% ammonium thioglycollate were prepared at pH 9.5. The solutions were clear and remained clear on lowering the pH to 5.

EXAMPLE 5

The cross-linking/polymerisation potential of the cystine-silicone copolymer was demonstrated as follows. 1 g of the copolymer solution was weighed into a 250 ml glass beaker and dried to a film in an oven at 6° C. for 4 hours. The beaker was cooled in a dessicator and then 250 ml of 10 buffer was added and stirred vigorously at 25° C. until no further copolymer dissolved (as evidenced by monitoring $A_{220}$). Only 12% of the copolymer was soluble, indicating polymerisation had occurred.

When cystine-silicone copolymer in its sulphite-reduced form was tested in a similar way cross-linking similarly occurred, with only 50% of the copolymer dissolving.

EXAMPLE 6

The potential for disulphide bond interchange with hair was demonstrated as follows. A set of 4 hairs was reduced with ammonium thioglycollate solution to achieve approximately 20%, 30%, 40% and 60% breakage, respectively, of the original disulphide bonds in the hair.. This was determined by studies on the mechanical behaviour of the hair.

Rinsing of the hair fibres, in their reduced state, with water at pH 9 had a negligible effect on bond reformation. In contrast, when treated with a 2% active solution of cystine-silicone copolymer, at pH 9, an increase in mechanical strength of the hair fibres equivalent to approximately 15% reformation of the original disulphide bonds in the hair was achieved. This indicates that the cystine-silicone copolymer penetrates hair and undergoes disulphide interchange with the hair fibres in their reduced state.

2% active cystine-silicone copolymer was included in a shampoo based on sodium lauryl ether sulphate and used to treat hair switches. The switches were treated with shampoo by rubbing the shampoo into the pre-wetted hair for one minute. The switches were then rinsed with lukewarm running water for 1 minute prior to assessment of wet comparability, which was markedly improved over that of the control switches.

Hair switches were treated with 1% active cystine-silicone copolymer and crosslinked by drying onto PTFE rollers. A tighter and shorter curl was produced compared to the control.

EXAMPLE 7

The potential for permanent setting of fabrics was demonstrated by treating wool fabrics with cystine-silicone copolymer, then steam pressing the fabrics. After this treatment the fabrics showed improved setting characteristics over the untreated control fabrics.

Whilst certain embodiments of the invention have been described above, it will be appreciated that modifications may be made.

We claim:

1. A copolymer comprising units made up of cystine, or a derivative thereof, bonded to a silicon-containing component, wherein the silicon-containing component contains at least one siloxane link.

2. A copolymer containing units of formula:

[—B—A—B'—]

where A is HN—CH($COOR_x$)$CH_2$—S—S—$CH_2$CH($COOR_y$)$NR_z$, $R_x$ and $R_y$ are the same or different and are hydrogen or an alkyl group, $R_z$ is hydrogen or an amino modifying group, and B and B' represent silicon-containing groups: wherein the units are linked together by siloxane bonds, the groups B and B' are the same or different, the group B in each unit is the same as or different from the group B in any other unit, and the group B' in each unit is the same as or different from the group B' in any other unit.

3. A copolymer according to claim 2, wherein the cystine or cystine derivative comprises 20 wt % to 70 wt % of the total weight of the polymer.

4. A copolymer according to claim 2, which has the structure:

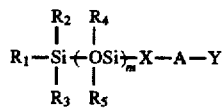

where:

X is a link group resulting from the reaction of an amino group on the cystine or cystine derivative with an amino reactive group on the silicon-containing group; R in the group A, is H or $CH_2CH_3$:

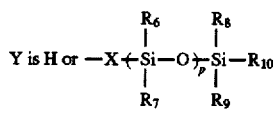

or an amino modifying group;

$R_1$ to $R_{10}$ are the same or different and are $CH_3$, OH or Z, where Z is one of:

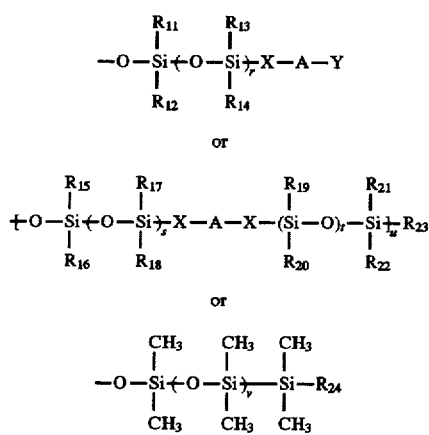

where $R_{11}$ to $R_{22}$ are the same or different and are $CH_3$, OH or Z, and $R_{23}$ and $R_{24}$ are $CH_3$ or OH, and m is from 0–100
p is from 0–100
r is from 0–100
s is from 0–100
t is form 0–100
u is from 0–100
v is from 0–100 and at least one of $R_1$ to $R_{10}$ is a Z group which contains an A group.

5. A copolymer according to claim 4, wherein X is —$(CH_2)_3$—O—$CH_2$—CH(OH)$CH_2$—.

6. A method of making a copolymer comprising reacting an organofunctional silicon-containing compound with at least one of the amino groups in cystine or a cystine derivative, and polymerising the reaction product of the silicon-containing compound and the cystine or cystine derivative.

7. A method according to claim 6, wherein the organofunctional silicon-containing compound has the structure:

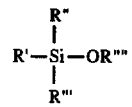

where: R' is a group containing an amino-reactive group capable of reacting with the amino group in the cystine or the cystine derivative, R" and R'" are the same or different and are an alkyl group or an alkoxy group or OH, R"" is hydrogen or an alkyl group.

8. A method according to claim 7, wherein R' is an epoxide group, a sulphonyl halide group, an aryl halide group, an anhydride group or an aldehyde group; and/or R" is $CH_3$ or $OCH_3$; and/or R'" is $CH_3$ or $OCH_3$; and/or R"" is $CH_3$ or $CH_2CH_3$.

9. A method according to claim 6, wherein the reaction of the organofunctional silicon-containing compound with the cystine or cystine derivative is carried out at a pH in the range 8 to 11.5, and at a temperature in the range 40° to 80° C.

10. A method of treating a keratin-containing substrate, comprising contacting keratin-containing substance with a solution of a copolymer according to claim 1, so that said copolymer is at least partially absorbed into said keratin-containing substance, and then further polymerising said copolymer to harden said copolymer.

11. The method of claim 10, wherein said copolymer is further polymerised by the removal of water.

12. A cosmetic formulation for treating keratin-containing substrates which comprises a copolymer as claimed in claim 1 in a cosmetically-acceptable carrier.

13. A cosmetic formulation according to claim 12, which comprises 0.1 wt % to 5 w % of the copolymer and one or more cosmetically-acceptable ingredients.

14. A method of treating a keratin-containing substrate, comprising contacting a keratin-containing substance with a solution of a copolymer according to claim 1, so that said copolymer is at least partially absorbed into said keratin-containing substance, and then further polymerising said copolymer to harden said copolymer.

15. The method of claim 11 wherein said copolymer is further polymerised by the removal of water.

16. A cosmetic formulation for treating keratin-containing substrates which comprises a copolymer as claimed in claim 2 in a cosmetically-acceptable carrier.

17. A cosmetic formulation according to claim 16, which comprises 0.1 wt % to 5 w % of the copolymer and one or more cosmetically-acceptable ingredients.

* * * * *

UNITED STATES PATENT AND TRADEMARK OFFICE
CERTIFICATE OF CORRECTION

PATENT NO. : 5,679,819
DATED : October 21, 1997
INVENTOR(S) : Jones et al.

It is certified that error appears in the above-identified patent and that said Letters Patent is hereby corrected as shown below:

Column 1, line 26, "vet" should read --wet--.

Column 2, line 4, "group's" should read --groups--.
           line 25, "residues can" should read --residues, can--.
           line 52, "one of" should read --one, of--.

Column 3, line 54, "or an alkoxy group or" should read --or an alkoxy group or OH.--.
           line 57, "illustrated by below." should read --illustrated by I-III below.--.

Column 4, line 66, "came" should read --same--.

Column 5, line 17, "treatment wool" should read --treatment of wool--.
           line 34, "68%" should read --60%--.

Column 6, line 4, "6°C" should read --60°C--.
           line 5, "250 ml of 10 buffer" should read --250 ml of pH 10 buffer--.
           line 48, "setting of fabrics" should read --setting of wool fabrics--.

Column 7, line 30, "different and" should read --different, and--.

UNITED STATES PATENT AND TRADEMARK OFFICE
CERTIFICATE OF CORRECTION

| | | |
|---|---|---|
| PATENT NO. | : | 5,679,819 |
| DATED | : | October 21, 1997 |
| INVENTOR(S) | : | Jones et al. |

It is certified that error appears in the above-identified patent and that said Letters Patent is hereby corrected as shown below:

Column 8, line 33 (second line of claim 10), "contacting keratin-containing" should read --contacting a keratin-containing--.

line 53 (first line of claim 15), "11" should read --14--.

Signed and Sealed this

Seventeenth Day of February, 1998

Attest:

BRUCE LEHMAN

*Attesting Officer*     *Commissioner of Patents and Trademarks*